United States Patent
Holtlund et al.

(10) Patent No.: US 7,374,943 B2
(45) Date of Patent: May 20, 2008

(54) HAEMOGLOBIN ASSAY

(75) Inventors: Jostein Holtlund, Olso (NO); Kerstin Bernström, Olso (NO); Ellen Dworsky, Olso (NO); Lise Corneliussen, Olso (NO)

(73) Assignee: Axis-Shield USA, Oslo (NO)

( * ) Notice: Subject to any disclaimer, the term of this patent is extended or adjusted under 35 U.S.C. 154(b) by 772 days.

(21) Appl. No.: 10/474,505

(22) PCT Filed: Apr. 10, 2002

(86) PCT No.: PCT/GB02/01664

§ 371 (c)(1),
(2), (4) Date: Feb. 26, 2004

(87) PCT Pub. No.: WO02/086512

PCT Pub. Date: Oct. 31, 2002

(65) Prior Publication Data

US 2004/0137641 A1 Jul. 15, 2004

(30) Foreign Application Priority Data

Apr. 24, 2001 (GB) .................. 0110053.6

(51) Int. Cl.
*G01N 33/558* (2006.01)
(52) U.S. Cl. ....................... 436/66; 436/514

(58) Field of Classification Search ............... 436/536, 436/66, 161, 166, 175, 177, 815, 824, 539, 436/67; 540/128; 544/69; 546/13; 548/110, 548/405; 549/4, 213; 552/10; 562/7
See application file for complete search history.

(56) References Cited

U.S. PATENT DOCUMENTS

| | | | |
|---|---|---|---|
| 5,242,842 A | * | 9/1993 | Sundrehagen ............... 436/536 |
| 5,631,364 A | * | 5/1997 | Sundrehagen et al. ...... 540/128 |
| 5,739,318 A | | 4/1998 | Frantzen et al. ............. 540/128 |
| 5,866,428 A | * | 2/1999 | Kim et al. .................... 436/66 |

FOREIGN PATENT DOCUMENTS

FR     2 749 853 A     12/1997

* cited by examiner

*Primary Examiner*—Alexa Neckel
*Assistant Examiner*—Imran Akram
(74) *Attorney, Agent, or Firm*—Bacon & Thomas PLLC

(57) ABSTRACT

The invention provides a kit for a glycated haemoglobin assay, said kit comprising: a porous membrane capable of retaining precipitated haemoglobin; a first reagent comprising zinc ions in aqueous basic solution or comprising a water soluble zinc compound; a second reagent comprising a chromophore-boronic acid conjugate; and optionally, an aqueous washing reagent; wherein at least one of the first and second reagents further comprises a surfactant capable of lysing erythrocytes, and wherein said second reagent if liquid is acidic.

10 Claims, 2 Drawing Sheets

HAEMOGLOBIN ASSAY

This invention relates to improvements in and relating to methods of assaying for glycated haemoglobin.

Proteins in solution in body fluids are continually subject to glycosylation processes. Glucose reacts with the proteins by non-enzymatic reactions to form glycoproteins, and in many cases the level of glycoprotein formation is proportional to the glucose concentration in the body fluid in question. For proteins not initially synthesized as glycoproteins, the fraction of a protein present in glycated form is therefore a function of the life-time of the protein in the organism and the glucose concentrations to which the protein has been exposed.

Unlike measurements of glucose concentrations in blood, plasma or urine, which only give information about the glucose concentration at the time of sampling, the amount of a protein present in glycosylated form gives an indication of the organism's control of glucose concentration over longer periods of time.

Erythrocytes (red blood cells) have a mean lifetime of approximately 120 days and contain large amounts of haemoglobin. The fraction of erythrocyte haemoglobin in glycosylated form is thus a good measure of the control of the disease in patients with diabetes mellitus, and is a function of the glucose concentrations in the blood of the patient in the weeks prior to the blood sampling.

In U.S. Pat. No. 5,242,842 (Axis) it was proposed to assay for glycosylated haemoglobin using as a reporter-labelled reagent a boronic acid conjugate, e.g. a conjugate of N-(resorufin-4-carbonyl)piperidine-4-carboxylic acid-N-hydroxysuccinimide ester (RESOS) or fluorescein isothiocyanate (FITC) with aminophenyl boronic acid. The anionic $B(OH)_3^-$ component of the reagent binds to the cis-diol groups of the glycosylated haemoglobin so labelling the glycosylated haemoglobin with the reporter label (e.g. RESOS or FITC).

In U.S. Pat. No. 5,631,364 (Axis), a group of particularly effective reporter-labelled boronic acid conjugates were described, including the xylene-cyanole-phenyl boronic acid conjugate referred to therein as XC-DAPOL-CPBA. The chromophore label gives this conjugate an absorption maximum at 616 nm (i.e. it is blue in colour) and the proportion of haemoglobin in a sample that is glycosylated can be determined by measuring sample absorbance at 616 nm and at 415 nm, where haemoglobin has an absorption maximum.

A diagnostic assay for glycated (i.e. glycosylated) haemoglobin using this system is available commercially from Axis-Shield Plc as the NycoCard® HbA1c test. In operation of this test a slightly alkaline aqueous reagent solution is mixed with a blood sample and the mixture is applied to a porous membrane which is rinsed before light reflectance by the membrane (i.e. by the haemoglobin trapped on the membrane) is determined. The reagent solution comprises a surfactant (to lyse the erythrocytes and release haemoglobin), XC-DAPOL-CPBA to bind to glycated haemoglobin and zinc ions to precipitate the haemoglobin. The precipitated haemoglobin, both glycated and non-glycated is caught by the membrane while other glycated proteins and excess boronic acid conjugate are washed off the membrane by the rinsing step.

The results for this assay however can vary with the storage time of the reagent, becoming unreliable if it is stored for about 6 months or more. Since a clinical laboratory may have test kits of varying ages, there is thus a need to increase the reproducible accuracy of a boronic acid conjugate-based glycated haemoglobin assay.

We have now found that the reliability of such assays can be improved if the boronic acid conjugate and the zinc are present in separate reagents in the assay kit.

Figure 1:
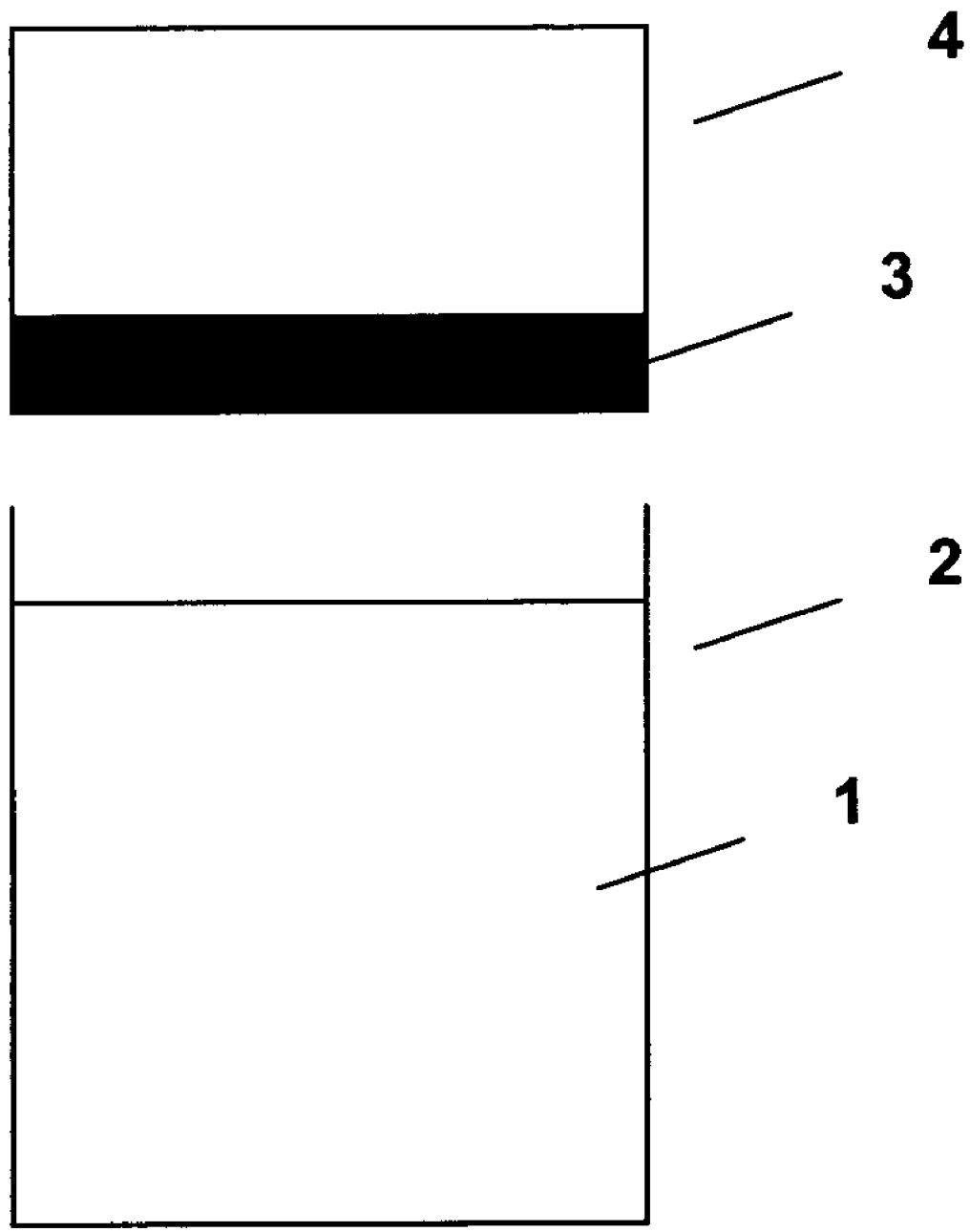
FIG. 1 is a schematic illustration of kit in which one of the reagents is in dried form.

Thus viewed from one aspect the invention provides a kit for a glycated haemoglobin assay, said kit comprising:

a porous membrane capable of retaining precipitated haemoglobin;

a first reagent comprising zinc ions in aqueous basic solution or comprising a water-soluble zinc compound;

a second reagent comprising a chromophore-boronic acid conjugate; and optionally, an aqueous washing reagent; wherein at least one of the first and second reagents further comprises a surfactant capable of lysing erythrocytes, and wherein said second reagent if liquid is acidic.

The second reagent in the kit of the invention may be a solution or a dried or solvent-free material. This reagent preferably comprises at least part of the surfactant. The solvent, where the reagent is liquid, may be water or a water-miscible organic solvent, e.g. an alcohol, ether, ketone, amide, sulphoxide, etc., or a mixture of two or more of these. Preferred examples of solvents are water, methanol, DMSO and formamide. The reagent preferably includes an acid (e.g. citric acid) and preferably has a pH below 6, more preferably below 5, if it is liquid. If the reagent is dried or solvent-free it is especially preferred that it be prepared by drying a solution for which the solvent is water, methanol, or methanol and water (preferably up to 70% by volume methanol, e.g. at least 20%, for example 30 to 70%). The use of water as the solvent is particularly preferred. It has been surprisingly been found that drying such a solution containing the boronic acid conjugate and surfactant, e.g. by evaporation, leaves an oily residue which is more rapidly dissolved in water than the conjugate or surfactant alone. Moreover, where a methanol/water system is used it is found that the residue is capable of giving more uniform coating to a surface than is the case with methanol alone. The results are even better when water alone is used as the solvent. It may be noted that it has long been known to be problematical to dry surfactant solutions with the result generally being a clumpy, porridge-like residue and this ability to produce a uniform, rapidly water-dispersible residue is most surprising.

The addition of a water-soluble macromolecule which does not interfere with the haemoglobin assay, eg a protein such as albumin (for example bovine serum albumin), in the production of the second reagent in dry or solvent-free form has been found to be especially beneficial as the dried residue is found to be more uniform, especially when after long periods of storage. The inclusion of such a macromolecule is also beneficial when the second reagent is in liquid form as it reduces incidence of conjugate precipitation. Moreover its inclusion in either the first reagent or the second reagent or both has been found to shorten the time required for uniform mixing of the first and second reagents. As a result, it is preferred that either or both of the first and second reagents contain such a macromolecular compound, in particular BSA at a concentration of up to 1% w/v, especially 0.025 to 0.3% w/v, more especially 0.05 to 0.1% w/v.

The boronic acid conjugate may for example be any of the chromophore-boronic acid conjugates described in U.S. Pat. Nos. 5,242,842, 5,631,364 and 5,739,318; however XC-DAPOL-CPBA is preferred.

The surfactant used in the reagents may be any surfactant capable of lysing erythrocytes, e.g. deoxycholates, Tritons and Tweens; however non-ionic surfactants such as Tritons, in particular Triton X-100 are preferred.

The first reagent may be a basic aqueous solution or may be dissolvable in water or an aqueous base to produce a basic aqueous solution. In the second case it may be a dried aqueous solution which simply requires reconstitution with water.

The first reagent preferably also comprises surfactant, and may contain other optional components, for example inorganic salts (e.g. sodium or magnesium chloride and sodium azide), glycine and buffering compounds. The zinc is preferably introduced as an inorganic salt, e.g. the chloride. The primary solvent is preferably water, but other water-miscible solvents may be present. The reagent's pH is basic, preferably weakly basic, e.g. 7.1 to 8.5, preferably 8.0 to 8.2, especially about 8.1. The pH however should be such as to make the mixture of the first and second reagents basic when the two are combined.

The first reagent preferably contains 5 to 30 mM, especially 7 to 20 mM zinc, and 0.05 to 0.22 w/v surfactant and is preferably buffered to pH 7.8 to 8.2.

The second reagent, if an aqueous liquid preferably contains 0.15 to 0.75 mg/g, especially 0.20 to 0.50 mg/g conjugate, and 0.05 to 0.25% w/v, especially 0.1 to 0.2% w/v, surfactant, and 5 to 20% v/v, especially 10 to 15% v/v water-miscible organic solvent (e.g formamide or DMSO), and if dried it is preferably formed from an aqueous solution containing 0.1 to 0.5 mg/mL, especially 0.1 to 0.4 mg/mL. more especially 0.15 to 0.3 mg/mL conjugate, 0.1 to 0.5% w/v, especially 0.25 to 0.4% w/v surfactant, 0.2 to 0.6 mM, especially 0.4 to 0.55 mM acid (e.g. citric acid), up to 70% v/v, preferably 0 or up to (e.g. 1% v/v upwards) to 50% v/v methanol, and preferably 0.025 to 0.3% w/v, especially 0.05 to 0.1%, BSA.

The washing reagent is conveniently an aqueous buffer, e.g. Hepes. A particularly suitable washing reagent comprises 50 mM morpholine, 200 mM NaCl, 0.5% w/v Triton-X-100, 0.1% w/v glycerol, 0.05% w/v $NaN^3$, pH 9.1.

The membrane used in the kit of the invention can be any suitably pore-sized membrane; however it is conveniently a glass fibre or borosilicate filter or a cellulosic membrane, e.g. with a "pore size" of 0.5 to 1.5 µm, especially 0.8 to 1.0 µm. Desirably an absorbent layer, e.g. a cellulosic layer or a polyether sulphone layer, is disposed against the membrane on the surface remote from the sample application surface and this will serve to draw the sample and reagents through the membrane by capillary action.

Figure 2:
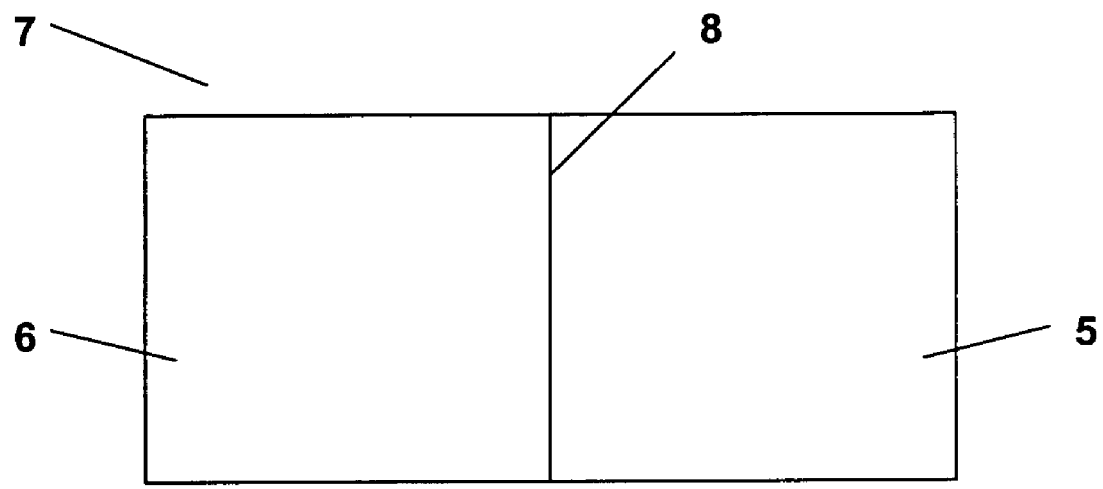
FIG. 2 is a schematic illustration of a kit in which the reagents are separated by a frangible membrane.

In the kit of the invention, as illustrate in FIG. 2. the first and second reagents (5,6) (where the second reagent is liquid) are preferably disposed in a two chamber container (7) with a frangible membrane (8) separating the chambers. This may for example take the form of a breakable (e.g. glass) container disposed inside a flexible container. Breaking the frangible membrane separator (e.g. the wall of a glass vial) allows the two reagents to be mixed before being brought into contact with the blood sample. Where the second reagent is a dried material (3), as illustrated in FIG. 1, it is preferably present in the kit coated onto the base and/or walls of a container or a stopper (4). In this way the first reagent can be filled into the second reagent's container (2) to bring the conjugate into solution for the assay or a stopper coated with dried second reagent (3) can be placed in the neck of a vial (eg a prefilled vial) of liquid first reagent (1). The second reagent if liquid can be used correspondingly to bring a dried first reagent into solution for use in the assay.

Reagent containers in the kit as supplied should desirably be capped to prevent liquid loss or moisture ingress.

In a further aspect, the invention also provides a method for assaying a blood sample for glycated haemoglobin, said method comprising contacting a blood sample with a surfactant capable of lysing erythrocytes, a chromophore-boronic acid conjugate, and zinc ions in aqueous solution, allowing the sample to incubate, passing the incubated sample through a porous membrane capable of retaining precipitated haemoglobin, flushing the membrane to remove conjugate not coupled to haemoglobin, measuring light reflected from the membrane at wavelengths at which haemoglobin and the conjugate respectively absorb light, and comparing the measured reflected light intensities whereby to provide a indication (e.g. a quantitative, semi-quantitative or qualitative indication) of the proportion of haemoglobin in the blood sample which is glycated, characterised in that said conjugate and zinc ions are brought together by combining a first reagent comprising zinc ions in aqueous basic solution and a second reagent comprising a chromophore-boronic acid conjugate wherein at least one of said first and second reagents further comprises a surfactant capable of lysing erythrocytes, and wherein said second regent if liquid is acidic.

Clearly the kit of the invention may be used in the assay method of the invention.

As mentioned above, the combination of surfactant and conjugate is more readily water soluble than the surfactant or conjugate alone. Thus viewed from a further aspect the invention provides a water-soluble material produced by drying a solution (e.g. an aqueous, alkanolic or aqueous-alkanolic solution) of an unsaturated cyclic organic acid (e.g. one having a molecular weight of 500 to 1500 D, for example a boronic acid conjugate) and a surfactant (e.g. a non-ionic surfactant, especially a Triton). Such a solution may of course contain further solutes which would likewise be released when the material is contacted with water.

The invention will now be described further with reference to the following non-limiting Examples.

The drying conditions for the second reagent in Examples 2, 5 and 6 and for the solutoin precursor in Example 3 are as follows:

A vacuum drying oven or a freeze-drier with a programmable vacuum controller can be used. The apparatus should be set to approach a pressure of 7-10 mbar within 40-65 minutes. Depending on the number of tubes (amount of liquid) to be dried and the kind of freeze-dryer, the setting will vary. The settings may thus be varied so as to produce an even film of dried material on the plastic walls.

For a Heraeus Vacuum Drying oven (VT 6025) the following settings have been used (400-500 tubes):

Temperature: 30° C.
Time to obtain P2: 5 min
P2: 100 mBar
Time to rest at P2: 5 min
Time to obtain P3: 5 min
P3: 50 mBar
Time to rest at P3: 5 min
Time to obtain P4: 5 min
P4: 20 mBar
Time to rest at P4: 5 min
Time to obtain P5: 10 min
P5: 7 mBar
Time to rest at P5: 804 min

EXAMPLE 1

Two Solution Assay

First Reagent
The first reagent comprises:

| | |
|---|---|
| 200 mM | Hepes buffer |
| 50 mM | glycine |
| 18 mM | $ZnCl_2$ |
| 30 mM | $MgCl_2$ |
| 400 mM | NaCl |
| 0.15% w/v | Triton X-100 |
| 0.05% w/v | $NaN_3$ |
| pH | 8.12 |

The reagent is prepared by mixing 1 mL 1M Hepes, 0.25 mL 1M glycine, 2 mL $H_2O$, 0.09 mL 1M $ZnCl_2$, 0.15 mL 1M $MgCl_2$, 0.4 mL 5M NaCl, 0.075 mL 10% Triton X-100 and 0.025 mL 10% $NaN_3$. The pH is adjusted to 8.12 and water is added to 5 mL.

The first reagent may alternatively be made as follows: 24.6 mg zinc chloride is dissolved in 2.5 mL water. 233.8 mg sodium chloride, 61 mg magnesium chloride hexahydrate, 0.05 mL 10% sodium azide and 0.1 mL 10% Triton X-100 are dissolved in 2.5 mL water. The two solutions are then combined. 476.6 mg HEPES and 37.6 mg glycine are dissolved in 1.5 mL water and 0.4 mL 5M sodium hydroxide. This HEPES solution is then added to the zinc and Triton X-100 solution and the pH is adjusted to 8.1 and the volume to 10 mL.

Second Reagent
The second reagent comprises:
12.4% v/v formamide
0.32 mg/mL XC-DAPOL-CPBA
0.15% w/v Triton X-100

The reagent is prepared by mixing 0.11 mL formamide, 0.52 mL XC-DAPOL-CPBA (3.15 g/L in formamide) and water to 5 mL. DMSO may be used in place of formamide.

Assay Procedure:
100 μL of the first reagent is mixed with 100 μL of the second reagent. The mixture is added to 5 μL blood and allowed to incubate for 2 minutes. A 25 μL aliquot is then placed on a glass fibre filter. 25 μL of a washing solution pH 9.1 (Example 4) is added and the result is read on a NycoCard® reader at 632 and 476 nm.

EXAMPLE 2

Solution and Dried Conjugate Assay

First Reagent
The first reagent comprises:

| | |
|---|---|
| 100 mM | Hepes |
| 25 mM | glycine |
| 9 mM | $ZnCl_2$ |
| 15 mM | $MgCl_2$ |
| 200 mM | NaCl |
| 0.1% w/v | Triton X-100 |
| 0.05% w/v | $NaN_3$ |
| pH | 8.12 |

The reagent is prepared by mixing 1 mL 1M Hepes, 0.25 mL 1 M glycine, 2 mL $H_2O$, 0.09 mL 1M $ZnCl_2$, 0.15 mL 1M $MgCl_2$, 0.4 mL 5 M NaCl, 0.1 mL 10% Triton X-100 and 0.05 mL 10% $NaN_3$. The pH is adjusted to 8.12 and water is added to 10 mL.

The first reagent may alternatively be made as follows: 12.3 mg zinc chloride is dissolved in 2.5 mL water. 116.9 mg sodium chloride, 30.5 mg magnesium chloride hexahydrate, 0.05 mL 10% sodium azide and 0.1 mL 10% Triton X-100 are dissolved in 2.5 mL water. The two solutions are then combined. 238.3 mg HEPES and 18.8 mg glycine are dissolved in 1.5 mL water and 0.2 mL 5M sodium hydroxide. This HEPES solution is then added to the zinc and Triton X-100 solution and the pH is adjusted to 8.1 and the volume to 10 mL.

Second Reagent (A) Solution Precursor
The solution precursor comprises
64.1% v/v methanol
0.23 mg/mL XC-DAPOL-CPBA
0.336% w/v Triton X-100
0.48 mM citric acid.

The solution precursor is prepared by dissolving XC-DAPOL-CPBA in methanol 0.36 mg/mL. 2 mL of this are mixed with 105 μL 10% Triton X-100, 1 mL water and 15 μL 0.1 M citric acid.

(B) Second Reagent
150 μL of the solution precursor is evaporated.
The solution precursor may alternatively comprise
20% v/v methanol
0.3-0.5 mg/mL XC-DAPOL-CPBA
0.34% w/v BSA
0.336% w/v Triton X-100
0.4-0.6 mM citric acid to pH 4.1

The solution precursor is prepared by dissolving XC-DAPOL-CPBA in methanol 2.5 mg/mL. 2 mL of the solution is mixed with 4.8 mL 0.7% Triton X-100 and 2 mL 0.5% w/v BSA is added and the pH is adjusted to 4.1 with 0.1 M citric acid (ca 50-60 μL). Water is added to a volume of 10 mL. The amount of XC-DAPOL-CPBA used is adjusted to provide an optical density (OD) of 32.5 at 620 nm.

125 μL of this solution precursor is then vacuum dried to produce the second reagent.

Assay Procedure:
200 μL of the first reagent are mixed with the second reagent and then with 5 μL blood. The assay procedure is thereafter as in Example 1.

EXAMPLE 3

Dried Buffer and Liquid Conjugate Assay (A) Solution Precursor
The first reagent comprises:
50 mM Glycinamide hydrochloride
10 mM $ZnCl_2$
20 mM $MgCl_2$
200 mM NaCl
0.1% w/v Triton X-100
0.05% w/v $NaN_3$
pH 8.12

13.6 mg $ZnCl_2$ are dissolved in 2.5 mL water. 116.9 mg NaCl, 40.6 mg $MgCl_2$×6 $H_2O$, 0.05 mL 10% w/v $NaN_3$ and 0.1 mL 10% w/v Triton X-100 are dissolved in 2.5 mL water.

The two solutions are then mixed. 55.2 mg glycinamide is then dissolved in 1.5 mL water and 0.4 mL 5M NaOH and this solution is added to the zinc solution. The pH is adjusted to 8.1 and the volume to 10 mL.

(B) First Reagent
  200 μL of the solution precursor is vacuum dried.

Second Reagent
  The BSA-containing solution referred to in Example 2 as the solution precursor is used in a liquid form.

Assay Procedure:
  200 μL of the first reagent are mixed with the second reagent and then with 5 μL blood. The assay procedure is thereafter as in Example 1.

EXAMPLE 4

Washing Solution

The washing solution comprises:
50 mM morpholine
200 mM NaCl
0.5% w/v Triton X-100
0.1% w/v glycerol
0.05% w/v NaN$_3$.

The solution is prepared by mixing the components, adjusting to pH 9.1 and adding water to achieve the desired concentration.

EXAMPLE 5

Solution and Dried Conjugate Assay

The materials for the assay are prepared as in Example 2 except that the solution precursor is prepared by dissolving the boronic acid conjugate in 0.5 mM NaOH to 0.25 mg/mL. This requires 10 to 30 minutes stirring. 2 mL of the solution is then mixed with 0.05 mL 10% Triton X-100 and stirred for a further 10 minutes. The pH is then reduced to about 4.5 by addition of 0.01 mL 0.1M citric acid. The assay is performed as in Example 2.

EXAMPLE 6

Solution and Dried Conjugate Assay

The materials for the assay are prepared as in Example 2 except that the solution precursor is prepared by dissolving the boronic acid in 10 mM NaOH to 2.5 mg/mL. 2 mL of this are mixed with 4.8 mL 0.7% w/v Triton X-100. 2 mL 0.5% w/v BSA is added and the pH is adjusted to 4.1 with 0.1 M citric acid (50-60 μL). Water is added to a volume of 10 mL. The quantity of conjugate used is adjusted to provide an optical density at 620 nm of 32.5. The assay is performed as in Example 2.

The invention claimed is:

1. A kit for a glycated haemoglobin assay, said kit comprising:
  a porous membrane capable of retaining precipitated haemoglobin;
  a first reagent comprising zinc ions in aqueous basic solution or comprising a water soluble zinc compound; and
  a second reagent comprising a chromophore-boronic acid conjugate;
  wherein at least one of the first and second reagents further comprises a surfactant capable of lysing erythrocytes, said second reagent if liquid is acidic and the boronic acid conjugate and the zinc are present in separate reagents in the assay kit.

2. A kit as claimed in claim 1 further comprising an aqueous washing agent.

3. A kit as claimed in claim 1 wherein said first reagent comprises zinc ions in aqueous basic solution.

4. A kit as claimed in claim 1 wherein said second reagent contains a surfactant.

5. A kit as claimed in claim 1 wherein said second reagent is a dried material.

6. A kit as claimed in claim 1 wherein said first reagent contains a surfactant.

7. A kit as claimed in claim 1 wherein at least one of said first and second reagents contains albumin.

8. A kit as claimed in claim 1 wherein one of said first and second reagents is in liquid form in a container and the other of said first and second reagents is in dried form coated on a stopper applicable to said container.

9. A kit as claimed in claim 1 wherein said second reagent is liquid and said first and second reagents are disposed in a two chamber container with a frangible membrane separating the chambers.

10. A kit as claimed in claim 8 wherein the reagent coated on the stopper is the second reagent and contains albumin.

* * * * *